(12) United States Patent
Katura et al.

(10) Patent No.: US 7,150,717 B2
(45) Date of Patent: Dec. 19, 2006

(54) OPTICAL MEASUREMENT APPARATUS FOR A LIVING BODY

(75) Inventors: Takusige Katura, Hatoyama (JP); Atsushi Maki, Fuchu (JP); Masashi Kiguchi, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 400 days.

(21) Appl. No.: 10/764,561

(22) Filed: Jan. 27, 2004

(65) Prior Publication Data
US 2004/0184024 A1 Sep. 23, 2004

(30) Foreign Application Priority Data
Feb. 17, 2003 (JP) ............... 2003-037653

(51) Int. Cl.
*A61B 5/00* (2006.01)
(52) U.S. Cl. ..................... 600/504; 600/481
(58) Field of Classification Search ............. 600/504, 600/532, 310; 128/203.25, 204.18
See application file for complete search history.

(56) References Cited

U.S. PATENT DOCUMENTS

| | | | | |
|---|---|---|---|---|
| 2,099,841 A | * | 11/1937 | Connell | 128/205.12 |
| 4,166,454 A | * | 9/1979 | Meijer | 600/479 |
| 5,954,658 A | * | 9/1999 | Gorti | 600/504 |
| 6,536,429 B1 | * | 3/2003 | Pavlov et al. | 128/203.26 |
| 6,577,884 B1 | * | 6/2003 | Boas | 600/310 |
| 2002/0169385 A1 | * | 11/2002 | Heinonen et al. | 600/531 |
| 2004/0144383 A1 | * | 7/2004 | Thomas et al. | 128/204.18 |

FOREIGN PATENT DOCUMENTS

| | | |
|---|---|---|
| JP | 9-135825 | 11/1995 |
| JP | 2001-212115 | 2/2000 |
| JP | 2002-224089 | 1/2001 |

OTHER PUBLICATIONS

Yamashita et al., "Brain and Circulatory Blood Pressure are Adjusted by the Brain", Kyoritsu Publishing Company (1998), pp. 144-145.

* cited by examiner

*Primary Examiner*—Charles Marmor, II
*Assistant Examiner*—Karen E Toth
(74) *Attorney, Agent, or Firm*—Reed Smith LLP; Stanley P. Fisher, Esq.; Juan Carlos A. Marquez, Esq.

(57) ABSTRACT

Disclosed is an optical measurement apparatus for a living body to provide a means for measuring blood flow activity within a short time inside the body, even if the test subject cannot distinguish between the active task period and the rest period. An optical measurement apparatus for a living body comprises a light irradiating section, and a light detecting section for detecting light transmitting through or reflected from the interior of the body. The concentration of carbon dioxide gas taken into the body is controlled by the respiration of the test subject and the resulting change in output from the light detecting section is then evaluated.

3 Claims, 8 Drawing Sheets

OPTICAL MEASUREMENT APPARATUS FOR A LIVING BODY

PRIORITY CLAIM

This application claims priority under 35 U.S.C. § 119 to Japanese patent application P2003-037653 filed Feb. 17, 2003, the entire disclosure of which is incorporated herein by reference.

FIELD OF THE INVENTION

The present invention relates to an optical measurement apparatus for a living body, and relates in particular to an optical measurement apparatus for a living body for non-invasive measurement and imaging of blood and blood vessels within a living body, an apoplexy diagnosis support device, and an emergency medical examination device.

BACKGROUND OF THE INVENTION

Carbon dioxide gas is widely-known to have an extremely large effect on expansion of the blood vessels. Within a carbon dioxide range of 25 through 600 mmHg, the change in blood flow rate in the brain is nearly linear in response to carbon dioxide levels in the arterial blood (non-patent document 1, Yamashita and others, "Brain and circulatory blood pressure are adjusted by the brain" p. 144–145, Kyoritsu Publishing Company, (1998)). The interrelation of carbon dioxide concentration within the blood, and the blood flow rate has been applied to control the concentration of carbon dioxide during respiration (patent document 1, JP-A No. 224089/2002). This interrelation has been applied to measurement with PET for early stage diagnosis of apoplexy. PET (or positron emission tomography) is a technology for non-invasive measurement and imaging of blood and blood flow within a living body. In this method, radioactive isotopes are administered into the blood vessels as a contract medium for imaging. By then measuring the resultant radioactive emissions, the state of blood flow and other information can be measured. However, in order to minimize adverse effects on a living body from the radioactive isotopes utilized in the measurements, isotopes with a short radioactive half-life are used. This short isotope life span means that a cyclotron is required to manufacture these isotopes in the immediate vicinity.

Near-infrared light is widely used in measuring internal living body information in view of the high transmittance provided within the body (patent document 2, JP-A No. 135825/1997 and patent document 3, JP-A No. 212115/2001) By beaming light inside a living body, the light transmitting through the body can be measured and in this way non-invasive measurement of internal body information performed. Measurement of oxygen saturation levels within the blood is possible by making use of changes in the respiratory spectrum that are one optical characteristic resulting from receiving of oxygen by hemoglobin which functions as a receptor of oxygen. This process can also be used in measuring brain activity. The action of nerve cells is a basic element of brain activity. Brain activity can be measured by measuring the changes in the respiratory spectrum of hemoglobin that result from variations in blood flow and oxygen saturation that accompany this brain nerve cell activity.

When measuring physiological reactions such as brain activity, the measured values are often absolute values rather than relative values. In making use of significant measurements of physiological reactions, an effective technique is to compare a specific active state within the body (for example moving a finger), with a different state (for example, a resting state). To create a specific active state for action within the body during measurement, a "task period" where the test subject for example, moves a finger is established. For comparison purposes, a "rest period" is also established where the body is in a resting state. These task periods and rest periods are necessary for creating specific action states for dynamic response within the body. The test subject must be able to distinguish between these two states. Therefore, if the test subject for example is in a coma, then establishing these task periods and rest periods is impossible.

However, a specific action state within the body can also be passively measured. In order to measure a sleeping state for example, data from results obtained from measuring brain waves in a sleep state by techniques such as brain wave measurement can be sorted into task periods (REM {rapid-eye-movement} sleep time, etc.) and rest periods (deep sleep time, etc.). Therefore a specific active state within the body can be measured passively even when the subject is in a coma. However, this kind of measurement requires a long time since a sufficient amount of data must be acquired for analysis.

SUMMARY OF THE INVENTION

An object of the present invention is to provide for measuring brain activity within a short time even if the test subject cannot distinguish between active task periods and rest periods.

To measure blood flow activity within the body of the test subject, the present invention is comprised of one or multiple light irradiating sections for beaming light onto the test subject; and one or multiple light detecting sections for detecting light transmitting through the body or reflected from the interior of the body; a respiratory component mixed density control device for creating a state corresponding to a task period and rest period within the body regardless of whether the patient is aware of the state, by controlling the carbon dioxide gas concentration within the air breathed by the test subject; and a computer to analyze the optical signal detected in the light detecting sections.

DETAILED DESCRIPTION OF THE PREFERRED EMBODIMENTS (First Embodiment)

The first embodiment, a best mode, describes the case when the test subject is a patient with apoplexy. In treating apoplexy, finding in what part of the head the illness is present, and determining if the illness is a hemorrhage or ischemia must be determined.

Figure 1:
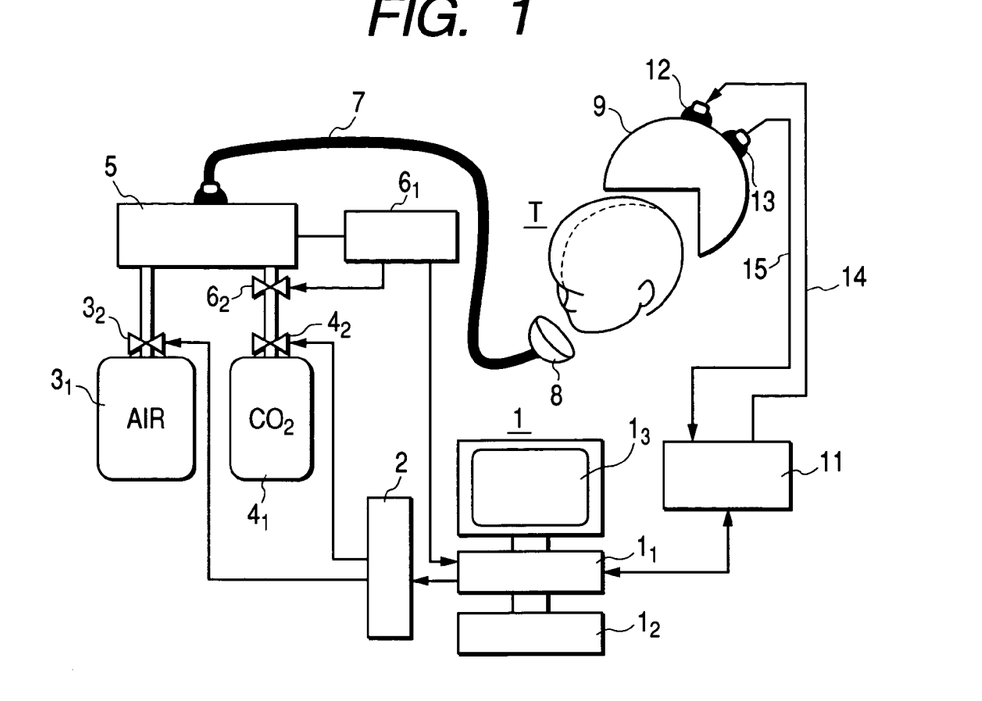
FIG. 1 is a block diagram showing an example of the specific device structure of the first embodiment.

FIG. 1 is a block diagram showing the structure of the device of the first embodiment. In FIG. 1, the test subject is denoted by T in the diagram. Reference numeral 1 denotes the control computer 1. The control computer 1 is comprised of a processor $1_1$, an operating section $1_2$, and a display $1_3$. The processor $1_1$ as described later on contains a control program for controlling the carbon dioxide gas concentration for test subject respiration and a program for optical measurement synchronized with the control program. The required control signals are output by this processor $1_1$ and these programs. Programs for analyzing the detected optical signals are also contained here. The images from keyboard operation are displayed on the operating section $1_2$, and peripheral equipment such as the mouse required for operating are contained here. Information such as control status of gas being supplied to the test subject T and the analysis results is shown on the display $1_3$. Reference numeral 2 denotes the gas valve control device. Reference numeral $3_1$ is the air tank and $3_2$ is the valve for that air tank $3_1$. Reference number $4_1$ is the carbon dioxide tank and $4_2$ is the valve for that carbon dioxide tank $4_1$. Reference numeral 5 is the gas mixer. The degree that the gas valve. $3_2$ and $4_2$ are opened is controlled by a signal from the processor $1_1$ of the computer 1 by way of the gas valve control device 2. Reference number $6_1$ is a gas concentration measurement device for carbon dioxide gas intake. When the constantly monitored carbon dioxide gas concentration in the gas mixer 5 exceeds a specified value, the emergency shutoff valve $6_2$ shuts off the carbon dioxide gas supplied from the gas mixer 5. The signal from the gas concentration measurement device $6_1$ is sent to the processor $1_1$ of the computer 1. The reference numeral 7 denotes a gas tube for supplying gas-supplied from the gas mixer 5. The reference numeral 8 denotes an inhale-exhale interface. This inhale-exhale interface 8 is a mask for supplying gas flowing from the gas tube 7 to the test subject T. Reference numeral 9 denotes a helmet body light measurement interface. Though not shown in the drawing, this helmet body light measurement interface 9 contains a light irradiating section for beaming light onto the mask covered head of the test subject T. This helmet body light measurement interface 9 also contains a light detection section for detecting light passing via the brain or light reflected within the brain. The reference numeral 12 denotes the irradiating light interface clamp and reference numeral 13 is the light detection interface clamp. These interface clamps are connected to the irradiating light section and light detecting sections inside the helmet body light measurement interface 9. Reference numeral 11 denotes the optical interface. This optical interface 11 generates an optical signal intensity according to the light irradiation signal sent from the processor $1_1$ of the computer 1, generates electrical signals according to the detected optical signal and sends the electrical signals to the processor $1_1$ of the computer 1. The reference numerals 14 and 15 respectively denote a light irradiating guide (optical fiber) and a light detecting guide (optical fiber) and connect the optical interface 11, irradiating light interface clamp 12 and light detection interface clamp 13.

Though not shown in the drawings since not directly related to the present invention, measurement devices such as for the test subject heartbeat rate, respiration count, blood pressure, oxygen saturation level in the blood and body temperature may be attached to the test subject. Besides collecting the required measurement data, these devices can provide displays and management functions for test subject safety.

Figure 2:
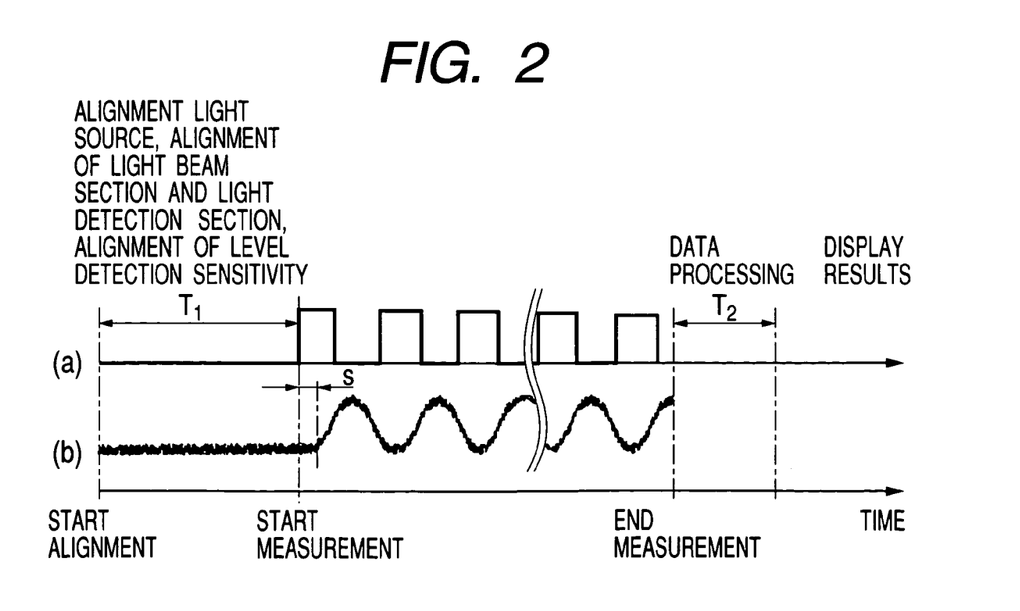
FIG. 2 is a chart showing the measurement procedure in the first embodiment.

FIG. 2 is a drawing showing the measurement procedure in the first embodiment. The horizontal axis shows the time. The vertical axis shows changes in carbon gas concentration over time in A and shows detected changes in light intensity in B.

The T1 period from the start of alignment is for aligning the light source. In other words, T1 is the period for alignment of the light source light intensity (irradiation light level) sent from the optical interface 11, and the light irradiating section and light detecting sections, and alignment of the light detection sensitivity level. In this period, the test subject T is placed in a resting state with the mask 8 attached. In other words, the operator starts alignment by making an entry on the operating section $1_2$, sending a control signal to the gas valve control device 2 from the processor $1_1$ to set the amount of opening of the gas valve $3_2$. The gas breathed by the test subject T is only natural air supplied from the air tank $3_1$. The signal applied to the optical interface $1_1$ of the processor $1_1$, by manual operation of operating section $1_2$ by the operator, or the alignment start signal applied to processor $1_1$ from operating section $1_2$, controls the power supply (not shown in drawing) voltage of the light source (not shown in drawing) inside the optical interface 11 by automatic operation in a pattern set beforehand. The intensity of the light irradiated onto the test subject from optical fiber 14 by the irradiating light interface clamp 12 is varied according to this voltage. The detected optical signal on the other hand is sent to the optical interface 11 from the optical fiber 15 by way of the light detection interface clamp 13. A detected optical signal to the display $1_3$, for example, shows the display according to the (light) intensity of the optical signal. The operator can adjust the light intensity by adjusting the voltage of the power supply (not shown in drawing) of the light source (not shown in drawing) in the optical interface 11. The sections where the light irradiating sections and light detecting sections within the helmet body light measurement interface 9 make contact with the test subject can also be adjusted at this time if necessary. A suitable light intensity (irradiation light level) from the light source for the test-subject T in a resting state can be established in this way.

After alignment is finished the measurement starts. The operator enters a signal on the operating section $1_2$ showing that alignment is finished so that a signal is sent from the processor $1_1$ controlling the amount of opening of the gas valve $4_2$ on the control valve device 2 according to the specified program, and the flow rate of carbon dioxide gas from the carbon dioxide gas tank $4_1$ into the gas mixer 5 is regulated. The carbon dioxide gas level (concentration) is increased or decreased by pulse control as shown in FIG. 2 while in this state. Consequently, the test subject T breathes air with carbon dioxide gas increased or decreased by pulse control instead of breathing natural air. When the test subject T breathes air with a high concentration of carbon dioxide gas instead of natural air, the amount of carbon dioxide gas dissolving into blood of the test subject T increases so there is a high concentration of carbon dioxide gas in the blood. Therefore as clearly shown in non-patent document 1, the flow rate of blood within the brain increases. This increase signifies the creation of a state the same as a test subject performing physical exercise. Reducing the concentration of carbon dioxide gas and letting the test subject breath natural air, reduces the brain blood flow rate and produces a state the same as the test subject resting state.

By increasing or decreasing through pulse control, the carbon gas concentration in the air breathed by the test subject in this way, states corresponding to task periods and rest periods within the body of the test subject can be created without the test subject being aware of the change in states. Consequently, as shown in FIG. 2, the pulses of the detected light intensity also increase or decrease according to the pulse increase or decrease in the carbon dioxide concentration. Here, the detected light intensity time is delayed versus the pulse-controlled increase/decrease in carbon dioxide gas concentration by a time equal to s. The smooth change is due to the delay in change in the amount (concentration) of carbon dioxide gas dissolving into the blood, and that this change is also smooth.

When the measurement ends after a specific time, the mask 8 of the test subject is removed. The collected data is then processed (time $T_2$) and the processed data displayed on the display $1_3$ of the control computer 1. Examples of data processing and its display are described later.

In view of individual differences in body functions of test subjects, in the present invention, measurement devices are attached to the test subject for measuring heartbeat rate, respiration count, blood pressure, oxygen saturation level in the blood and body temperature and the required measurement data is collected. Along with enhancing test subject safety in this way, a portion of the data from the current measurements serving as an indicator for time-based pattern changes in the carbon dioxide concentration, is combined with the carbon dioxide gas intake concentration measurement device $6_1$ signal. These measurement values and the carbon dioxide gas intake concentration measurement device $6_1$ signal are stored along with the basic measurement values in the control computer 1.

Next an example of the processing and display of the acquired time-based data is described. First of all, the time-based data for intake carbon dioxide gas concentration signal and light intensity signals taken from the start of measurement to the end of measurement as shown in FIG. 2, is subdivided into fixed periods set in advance by the user. A correlation is then calculated for each sub-division. The correlation can be calculated with equation (1).

$$f(D(t, u), R(t, u)) = \quad [\text{Equation 1}]$$

$$\frac{(u-t)\sum_{i=t}^{u} D(i, 1)R(i, 1) - \left(\sum_{i=t}^{u} D(i, 1)\right)\left(\sum_{i=t}^{u} R(i, 1)\right)}{\sqrt{\left\{(u-t)\sum_{i=t}^{u} D(i, 1)^2 - \left(\sum_{i=t}^{u} D(i, 1)\right)^2\right\} \cdot \left\{(u-t)\sum_{i=t}^{u} R(i, 1)^2 - \left(\sum_{i=t}^{u} R(i, 1)\right)^2\right\}}}$$

Here, D (t, u) is the detected light signal intensity of the subject T from time t to u, R is the intake carbon dioxide gas concentration signal for the same period. The Eq. (1), does not take the time delay s shown in FIG. 2 for the intake carbon dioxide gas concentration signal into account. However, a correlation taking this (time delay s) into account can be calculated by using Eq. (2).

$$f(D(t+s, u+s), R(t, u)) = \quad [\text{Equation 2}]$$

$$\frac{(u-t)\sum_{i=t}^{u} D(i+s, 1)R(i, 1) - \left(\sum_{i=t+s}^{u+s} D(i, 1)\right)\left(\sum_{i=t}^{u} R(i, 1)\right)}{\sqrt{\left\{(u-t)\sum_{i=t+s}^{u+s} D(i, 1)^2 - \left(\sum_{i=t+s}^{u+s} D(i, 1)\right)^2\right\} \cdot \left\{(u-t)\sum_{i=t}^{u} R(i, 1)^2 - \left(\sum_{i=t}^{u} R(i, 1)\right)^2\right\}}}$$

The user can here evaluate the measurement results and decide on the delay s.

The results can be displayed by various methods. The user can therefore select a method according to the particular objective.

Figure 3:
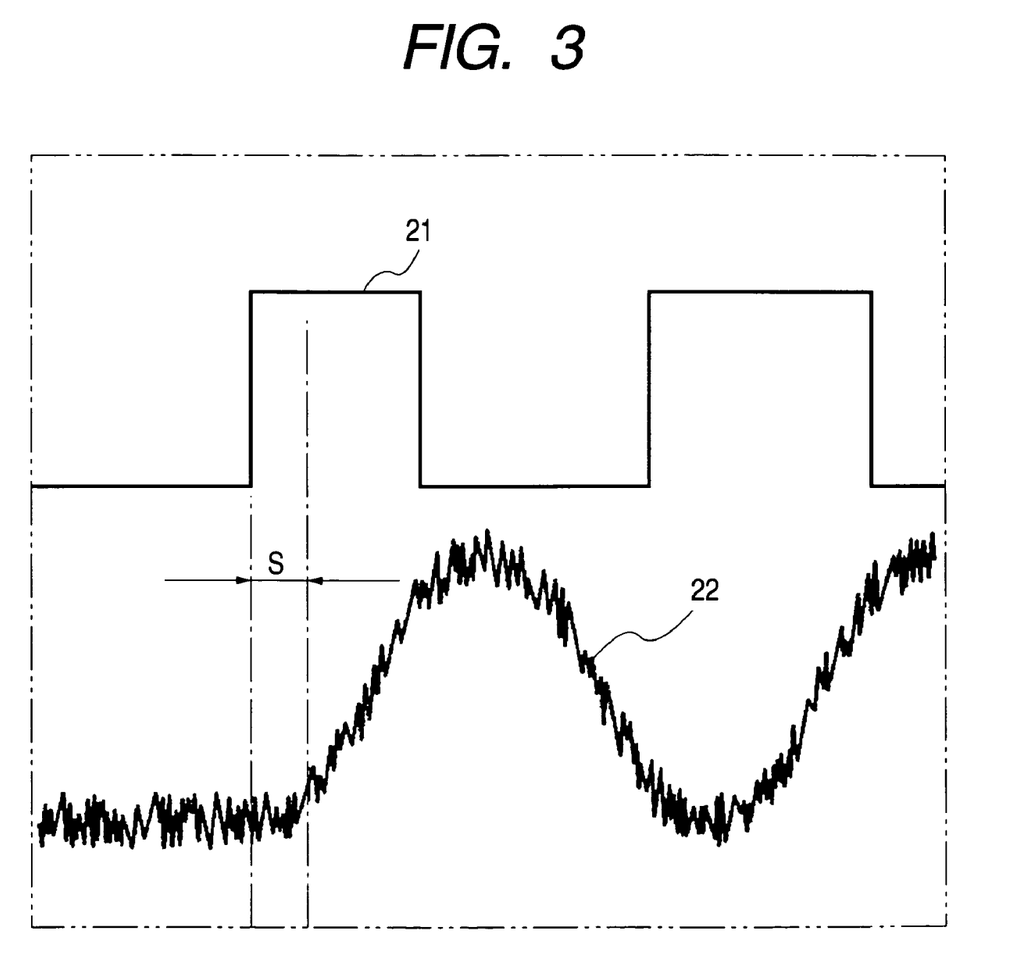
FIG. 3 is a graph showing a display of the variation 21 in inhaled carbon dioxide gas concentration signal and the variation 22 in the optical detection signal of the test subject T for one measurement point of the test subject T along a time axis.

(1) FIG. 3 is a graph showing a display of the variation 21 in the inhaled carbon dioxide gas concentration signal and the variation 22 in optical detection signal of the test subject T for one measurement point on the test subject T along a time axis. The data shown in FIG. 2 is taken along a long time-base (approximately 30 minutes or more). This long period of time makes it impossible to display unchanged and in detail the relation between the variation 22 in optical detection signal of test subject T versus the variation 21 in inhaled carbon dioxide gas concentration signal. By subdividing and displaying this into convenient time units, and then allocating and comparing at convenient time periods, the (activity) status of the body of test subject T can be seen in detail.

Figure 4:
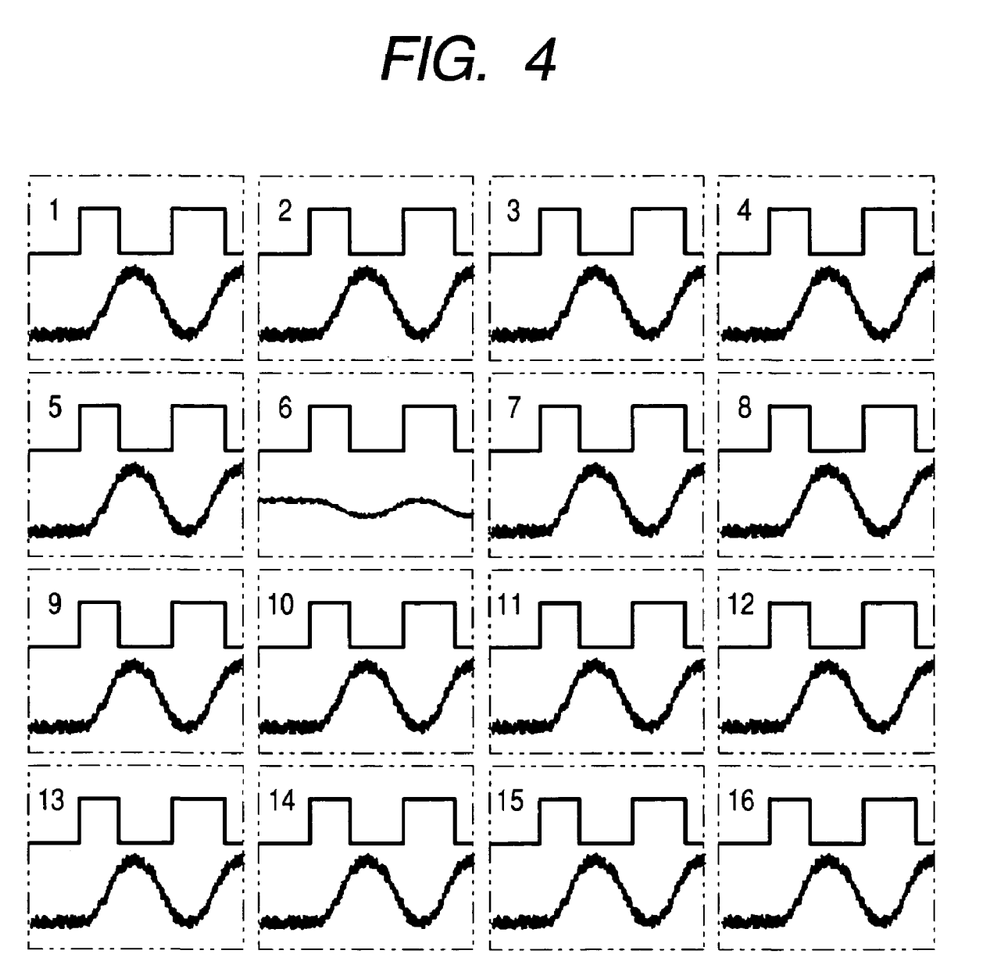
FIG. 4 is a graph showing the variation 21 in FIG. 2 in inhaled carbon dioxide gas concentration signal and the variation 22 in FIG. 2 in the optical detection signal of the test subject T along a time axis the same as in FIG. 3, however the display shows results measured simultaneously for 16 points (4×4) on the test subject T.

(2) FIG. 4 is a graph showing the variation 21 in the inhaled carbon dioxide gas concentration signal and variation 22 in optical detection signal of the test subject T along a time axis the same as in FIG. 3. ,However, the display shows results measured for 16 points (4×4) at the same time points on the test subject T. In this case, the data is arrayed to match the spatial placement of the measurement points. In the example in FIG. 4, of the 16 measurement points numbered from 1 to 16, only the sixth measurement point (or No. 6) shows no status for the variation 22 in optical detection signal of test subject T versus variation 21 of the inhaled carbon dioxide gas concentration signal. This display is due to a blood flow of nearly zero in the blood vessels at the position corresponding to measurement point No. 6.

Figure 5:
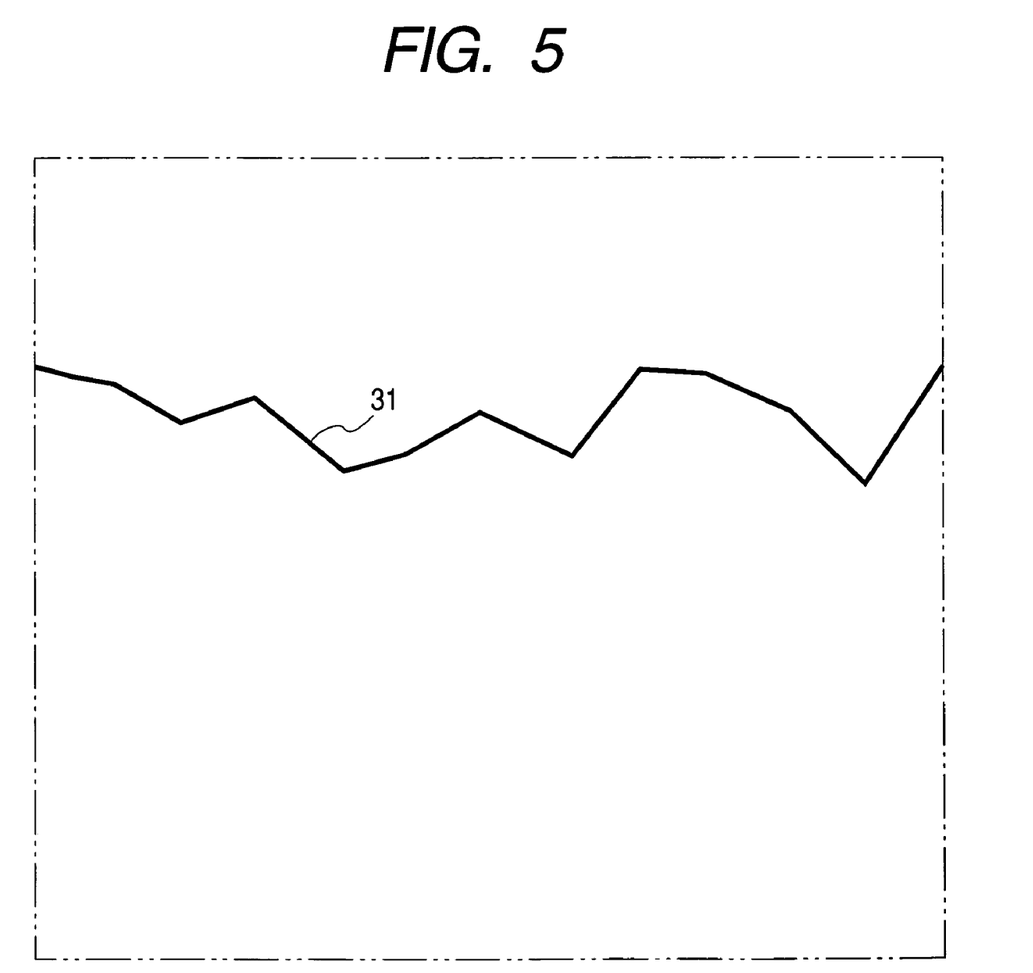
FIG. 5 is a graph showing the temporal change 31 in the optical detection signal intensity correlation along a time axis.

(3) FIG. 5 is a graph showing the temporal change 31 along a time axis in the correlation obtained in the previously described equations (1) or (2). In this case also, the display is shown after being calculated and subdivided into appropriate time units. If this display is then allocated and compared along convenient time periods, the (activity) status of the body of test subject T can be observed in detail.

Figure 6:
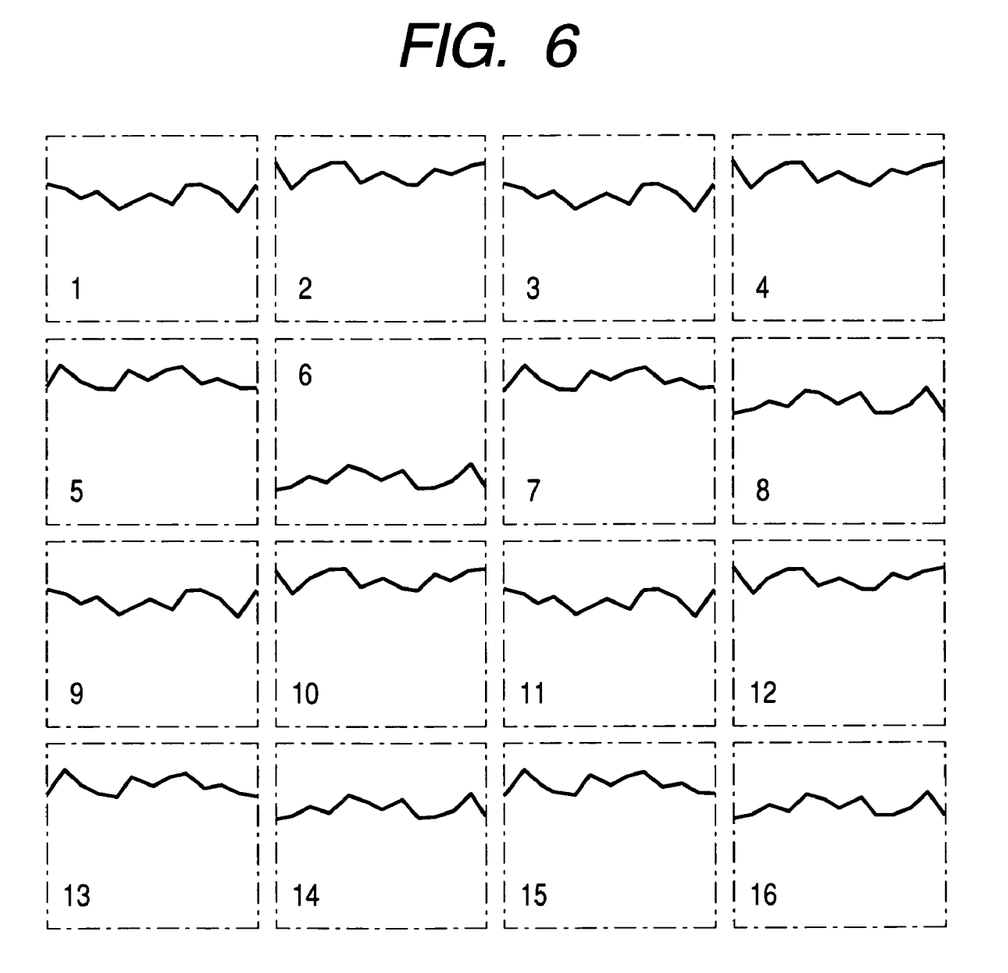
FIG. 6 is a graph showing a display of the variation 21 in FIG. 2 in inhaled carbon dioxide gas concentration signal and the temporal change 31 in the optical detection signal intensity correlation along a time axis, however the display shows results measured simultaneously for 16 points (4×4) on the test subject T.

(4) FIG. 6 shows the temporal change in the correlation of the variation 22 in optical detection signal intensity correlation to the variation 21 in the inhaled carbon dioxide gas concentration signal along a time axis the same as in FIG. 5. The display shows the measurement results for the same points when using 16 points (4×4) on the test subject T. The example in FIG. 6, also uses measurement points numbered from 1 to 16. Among these 16 measurement points, only the sixth measurement point (or No. 6) shows an extremely small temporal change in the correlation. This display is due to a blood flow of nearly zero in the blood vessels at the position corresponding to measurement point No. 6.

Figure 7:
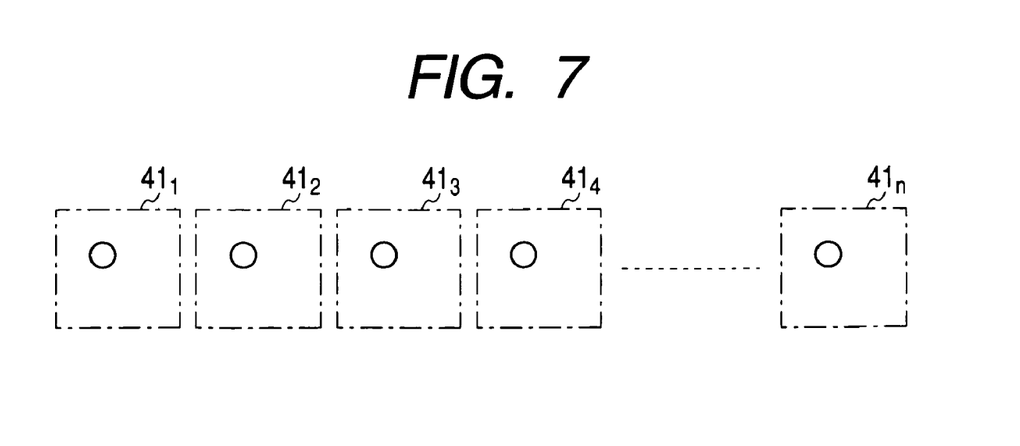
FIG. 7 is drawings showing the time classification sequence spanning the total measurement time for the signal intensity grouped in time units shown in FIG. 4 represented by color type and concentration.

The displays in FIG. 4 or FIG. 6 show results subdivided in appropriate time units. Displaying results spanning the total measurement time within the limited space of the display $1_3$ in control computer 1 is difficult. One display method usable in such cases is representing the signal intensity at the subdivided time units in color types and in concentrations and then arranging these in a sequence of time subdivisions spanning the total measurement time. FIG. 7 utilizes this concept, in a display where the signal intensities shown in FIG. 4 are repeatedly measured at all the measurement points. In FIG. 4, the signal intensity time units are shown subdivided into units of $41_1, 41_2, ---, 41_n$. FIG. 7 cannot offer a detailed view, however the sixth measurement point (or No. 6) shows that a low signal intensity continues at that point across the total measurement time. So after viewing this display, a detailed analysis can be made using the displays from FIG. 3 through FIG. 6.

The above explanation, described repetitively increasing or decreasing the time-based (change) pattern of the inhaled carbon dioxide gas level (or concentration) over a fixed period. However, the repeated increases or decreases in the time-based (change) pattern for the inhaled carbon dioxide gas level may be controlled to repeat multiple times within a specified period. In this case, if the body activity state of test subject T is the same, then the change in light signals detected from test subject T will repeat for those repeating periods. Therefore if a cumulative average of light signals detected from test subject T from a repeating period is utilized, then irregularities occurring in measurements in those repeating periods can be absorbed and reliable data obtained. In that case, the reliability level of the data is recorded as a cumulative count within the processor $1_1$, or may be shown on the display $1_3$. Also, rather than a simple cumulative average, those result may be utilized via processing with statistical examination methods.

(Second Embodiment)

Figure 8A:
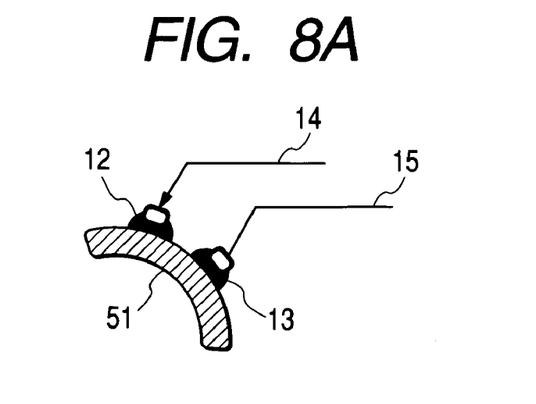
FIG. 8A is a drawing showing the optical measurement interface section made of flat plates of flexible material instead of the helmet-shaped optical measurement interface shown in FIG. 1.
Figure 8B:
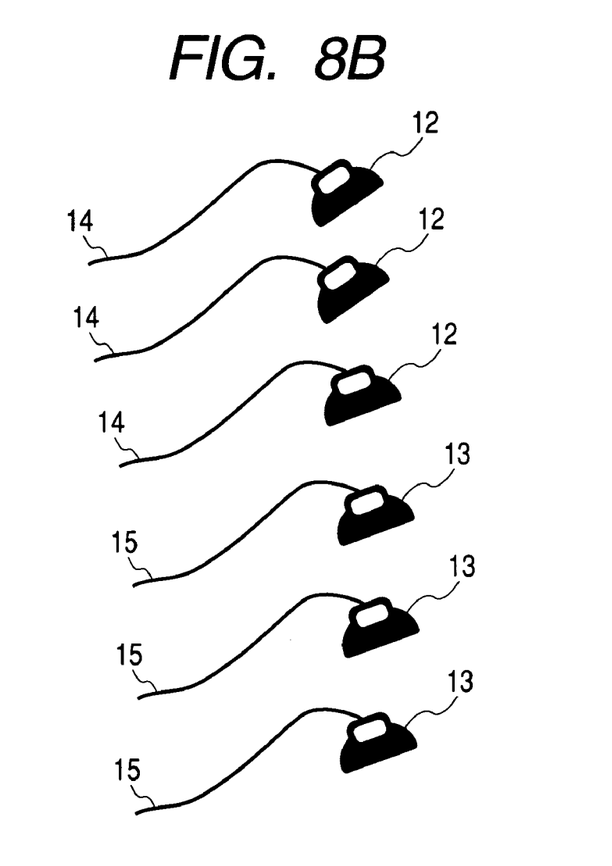
FIG. 8B is a drawing showing the light irradiating interface section and the light detection interface separated into multiple separate pieces.

The second embodiment is described next while referring to FIG. 8A and FIG. 8B. FIG. 8A is a drawing showing the optical measurement interface section 51 made of flat plates of flexible material instead of the helmet-shaped optical measurement interface shown in FIG. 1. The example in FIG. 8B is a drawing showing the light irradiating interface section 12 installed as multiple separate pieces. In this drawing, the light detection interfaces 13 are installed as multiple separate pieces corresponding to the light irradiating interface section 12. Using these types of separable components allows mounting the light measurement interface not only on the head but also all parts of the body of the test subject T. The response to changes in inhaled carbon dioxide gas concentrations is therefore not limited to brain diseases but can be applied to all parts of the living body for example, the head, hand, arms, legs, thighs, chest, stomach, back and buttocks, etc.

(Third Embodiment)

In the third embodiment, measurement values obtained from all parts of the head are integrated utilizing a device structure identical to the first embodiment.

To integrate the measurement values, the gas valve $4_2$ opening is regulated to change the carbon dioxide gas concentration in the gas mixer 5 in order to set the inhaled carbon dioxide gas concentration as one condition among multiple inhaled carbon dioxide gas concentrations set beforehand by the user. The signal from the gas concentration measurement device $6_1$ is evaluated to find if the carbon dioxide gas concentration from the gas mixer 5 has reached the specified value. After a specified preset time has elapsed, in order to await a change of carbon dioxide within the blood to a steady state resulting from changes in the inhaled carbon dioxide gas concentration, the light signal from the test subject T is detected again. The signal for the preset inhaled carbon dioxide gas concentration, and the light signal detected at this concentration, are stored in the processor $1_1$ as one set of data.

The signal for this preset inhaled carbon dioxide gas concentration, and the light signal detected at this concentration are repeatedly acquired as one set of data, while changing the inhaled carbon dioxide gas concentration. The processor $1_1$ can be programmed to set sufficient required conditions for changing the inhaled carbon dioxide gas concentration at this time.

Figure 9:
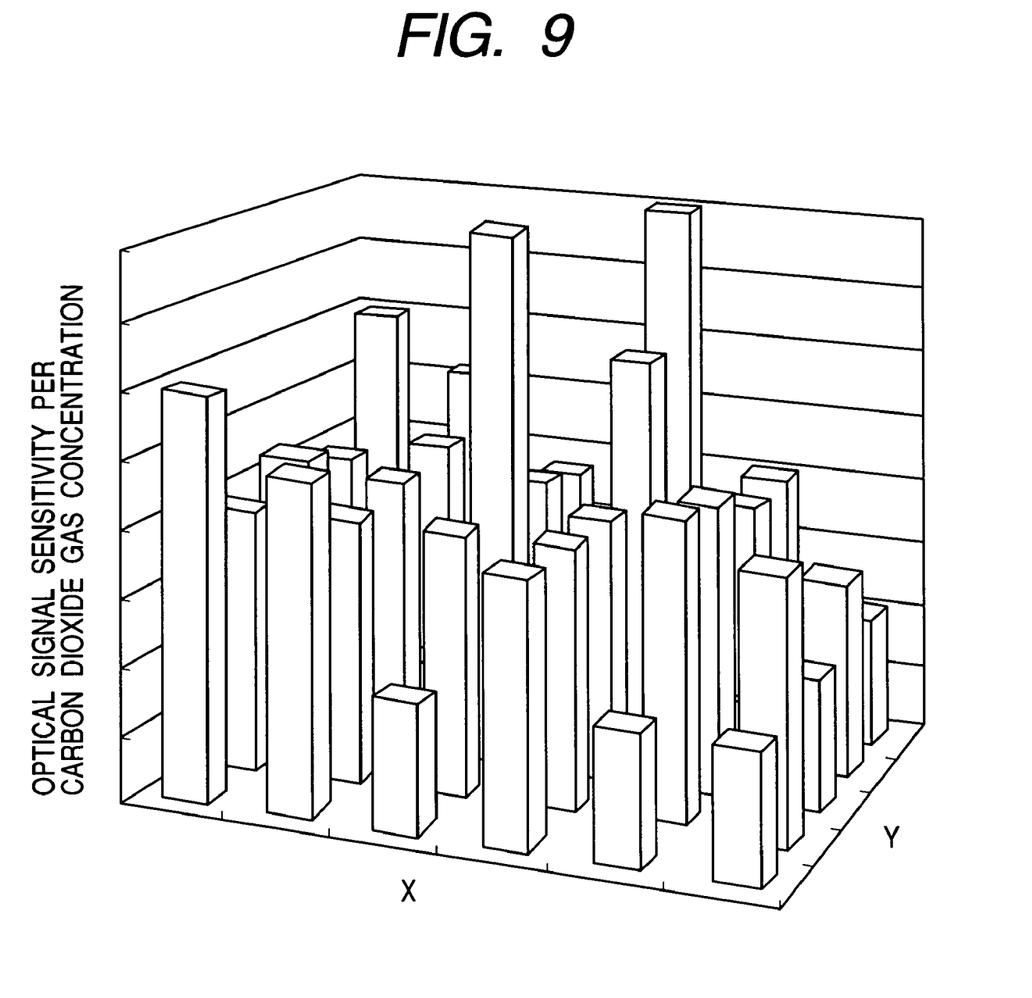
FIG. 9 is a graph showing the sensitivity distribution derived from data on the state of intake carbon dioxide gas concentration obtained from repeated measurements under the condition of programmed multiple intake carbon dioxide gas concentrations; and multiple groups of detected optical signals.

The intensity distribution of light signals in each part of the head are found from the sets of detected light signals and from data on the inhaled gas concentration obtained by repeated measurement under the multiple conditions for gas inhalation concentrations that were programmed into the processor $1_1$. These intensity distribution results are equivalent to the sensitivity distribution. An example of this type of sensitivity distribution is shown in FIG. 9. This data is stored in the processor $1_1$.

Figure 10:
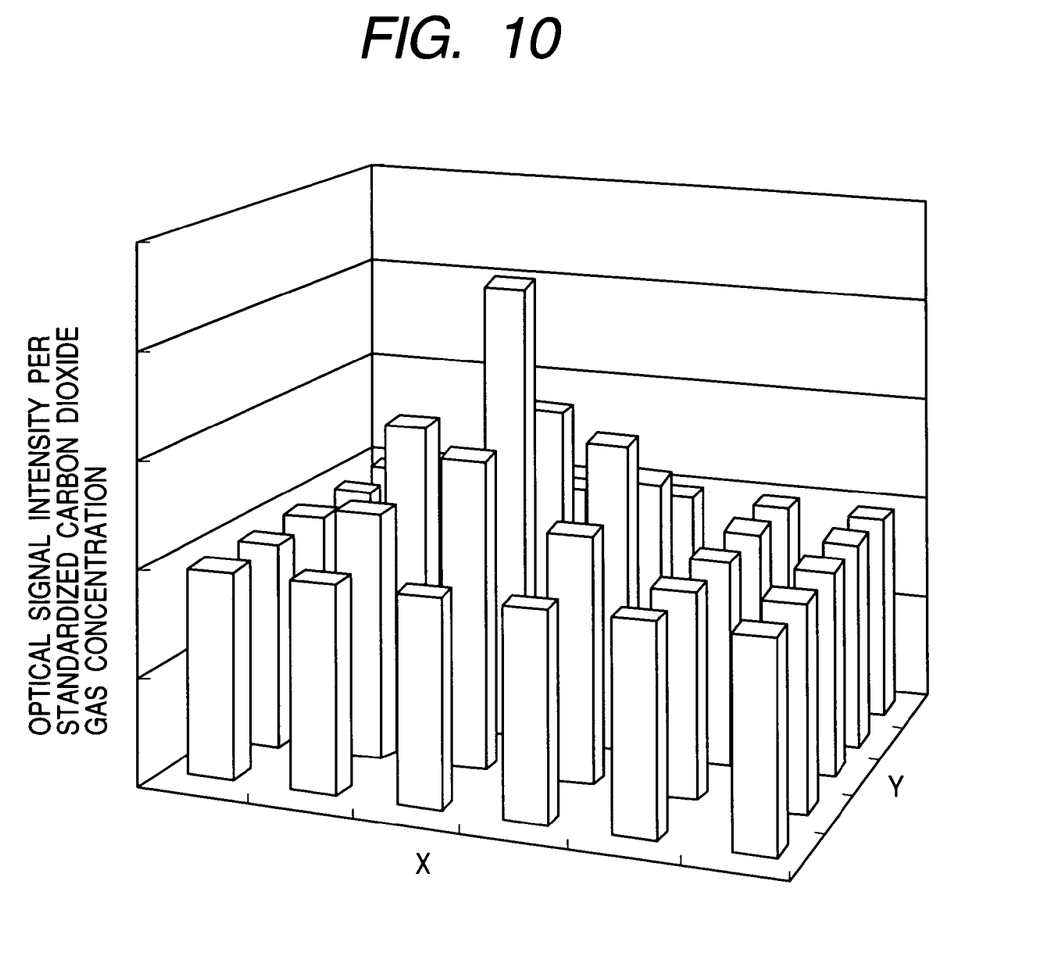
FIG. 10 is a graph showing integrated measurement results of data on the sensitivity distribution shown in FIG. 9 for measurement results of other test subjects obtained using the same program and same devices.

Measurement of other test subjects is next performed using the same apparatus and the same program. By integrating the results acquired from these measurements, to obtain the sensitivity distribution data shown in FIG. 9, measurement results not depend on sensitivity can be acquired in various measured sections. FIG. 10 is a drawing showing an example of integrating the measurement results.

OTHER EMBODIMENTS

The above embodiments all utilized measurements of the head in their descriptions. However, the present embodiment may be applied to measurements of all parts of the body.

In all of the above embodiments, the task periods and the rest periods were all set utilizing the inhaled carbon dioxide gas concentration. However, the task period may for example be a period where the test subject continually listens to a specified sound or music; and the rest period may be a period where the subject continually maintains a quiet state with the eyes closed.

The present invention therefore renders the effect that measurements can be made without the test subject being aware of or distinguishing between task periods and rest periods.

What is claimed is:

1. An optical measurement apparatus for use in examination of a living body test subject comprising:
    at least one light irradiating section configured to beam light onto the body of the living body test subject;
    at least one light detecting section configured to detect light configured to transmit through the body or reflected from the interior of the body;
    a carbon dioxide gas concentration control device configured to create a first state in the body simulating a task period and a second state in the body corresponding to a rest period by controlling the carbon dioxide gas concentration applied within the air breathed by the test subject via the carbon dioxide gas concentration control device;
    and a computer configured to control the light irradiating section and the light detecting section, and set a light detection sensitivity level, and analyze light signals detected by the light detecting section, wherein said computer further comprises
    a display section configured to display variations in said carbon dioxide gas concentration over time, and variations in said detected light signal intensity over time.

2. An optical measurement apparatus according to claim 1, wherein said computer further comprises
    a display section configured to display variations in a correlation between said gas concentration and said light signal intensity over time.

3. An optical measurement apparatus according to claim 1, wherein said computer contains an integrating function unit configured to find a sensitivity distribution based on measurement values obtained by changing test subject carbon dioxide gas concentrations, and integrating measurement signals of the test subjects with said sensitivity distribution.

* * * * *